US00PP20012P2

(12) United States Plant Patent
Davis

(10) Patent No.: US PP20,012 P2
(45) Date of Patent: May 19, 2009

(54) SIBERIAN CYPRESS PLANT NAMED 'CONDAVIS'

(50) Latin Name: *Microbiota decussata*
Varietal Denomination: Condavis

(75) Inventor: Harold A. Davis, Chadds Ford, PA (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/071,395

(22) Filed: Feb. 20, 2008

(51) Int. Cl.
*A01H 7/00* (2006.01)

(52) U.S. Cl. ..... Plt./213

(58) Field of Classification Search ..... Plt./213
See application file for complete search history.

*Primary Examiner*—June Hwu
(74) *Attorney, Agent, or Firm*—Buchanan Ingersoll & Rooney PC

(57) ABSTRACT

A new and distinctive *Microbiota decussata* plant is provided. Unlike common plants of the species, the new plant displays attractive green foliage wherein the leaf scales are raised both when juvenile and mature so as to impart a fuzzy appearance. The growth habit is creeping and prostrate. The new plant is well suited for growing as a specimen plant or in a group as a ground cover.

2 Drawing Sheets

Botanical/commercial classification: *Microbiota decussata*/Siberian Cypress.
Varietal denomination: cv. Condavis.

SUMMARY OF THE INVENTION

The present invention is a new and distinct Siberian Cypress cultivar, botanically known as *Microbiota decussata*. *Microbiota* is recognized to be a genus of evergreen coniferous shrub in the cypress family Cupressaceae, containing only one species *Microbiota decussata*. Such species is believed to have originated in the Russian Far East, and sometimes is identified by the common names of Siberian Cypress, Cypress, and Russian arborvitae.

The new plant of the present invention was discovered as a naturally-occurring branch sport of unknown causation which appeared in a outdoor nursery under a hoop house setting on a common *Microbiota decussata* plant. The discovery was made during July, 2002, at West Grove. Pa., U.S.A. I was attracted to a single branch of a single plant of the species primarily in view of the distinctive appearance of the foliage which was unlike that of all other *Microbiota decussata* plants being grown in the nursery and otherwise known to me. The distinctive plant was carefully preserved and has thereafter undergone detailed observation and evaluation.

It was found that the new Siberian Cypress plant of the present invention displays the following combination of characteristics:

(a) displays a creeping prostrate growth habit, (b) forms attractive green foliage wherein the leaf scales are raised so as to impart a fuzzy appearance unlike the appressed leaf scales displayed by common *Microbiota decussata* plants, and (c) is well suited for growing as a specimen plant or in a group as a ground cover.

The foliage of the new cultivar of the present invention commonly assumes a greyed-orange coloration during the winter months.

The new cultivar can be readily distinguished from previously available *Microbiota decussata* plants upon an inspection of the foliage configuration. More specifically, the leaf scales of common *Microbiota decussata* plants are appressed and lie in a substantially flat arrangement with respect to stems. On the contrary the leaf scales of the new cultivar are substantially raised from the stems and impart a soft and fuzzy foliar appearance to the overall plant.

The new cultivar of the present invention can be grown to advantage to provide a distinctive ornamental plant which can be grown as a specimen in the landscape or in groups to provide a continuous ground cover.

Asexual reproduction of the new cultivar by the use of cuttings has been carried out at West Grove, Pa., U.S.A. Commonly such asexual reproduction has been carried out in the winter while using Hormodin No. 3 rooting hormone and the use of bottom heating at approximately 70° F. to promote faster rooting. Such propagation has confirmed that the unique combination of characteristics of the new cultivar has been stably established and is well transmitted to successive generations. The new cultivar asexually reproduces in a true-to-type manner.

The new cultivar has been named 'Condavis' and will be marketed under the FUZZBALL trademark.

BRIEF DESCRIPTION OF THE PHOTOGRAPHS

The accompanying photographs show as nearly true as it is reasonably possible to make the same in color illustrations of this character, typical container-grown specimens of the new cultivar at an age of approximately five years while being grown at West Grove, Pa., U.S.A. For the first five to six months, the plants had been grown indoors during which time root development took place. The plants thereafter had been placed in larger containers and were grown outdoors with the protection of a sheet of plastic during the winter.

DETAILED DESCRIPTION

Figure 1:
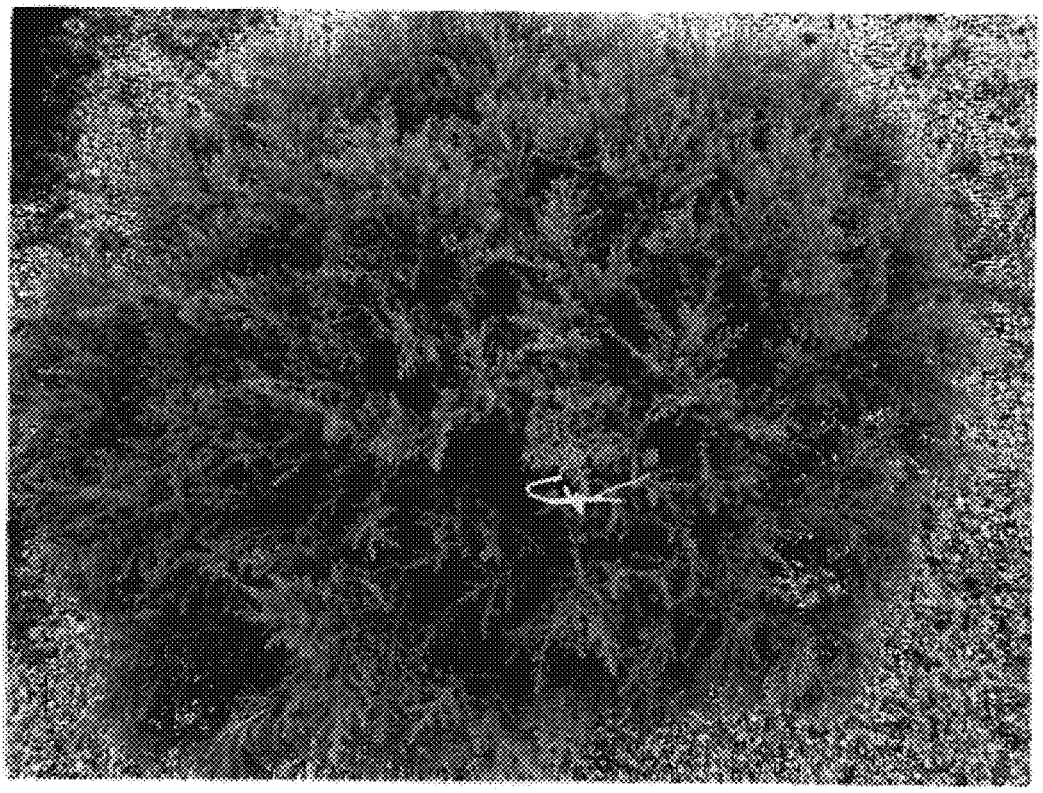
FIG. 1 shows from above a typical plant of the new cultivar during the summer wherein the attractive green coloration of the fuzzy foliage and the generally uniform growth habit are depicted.
Figure 2:
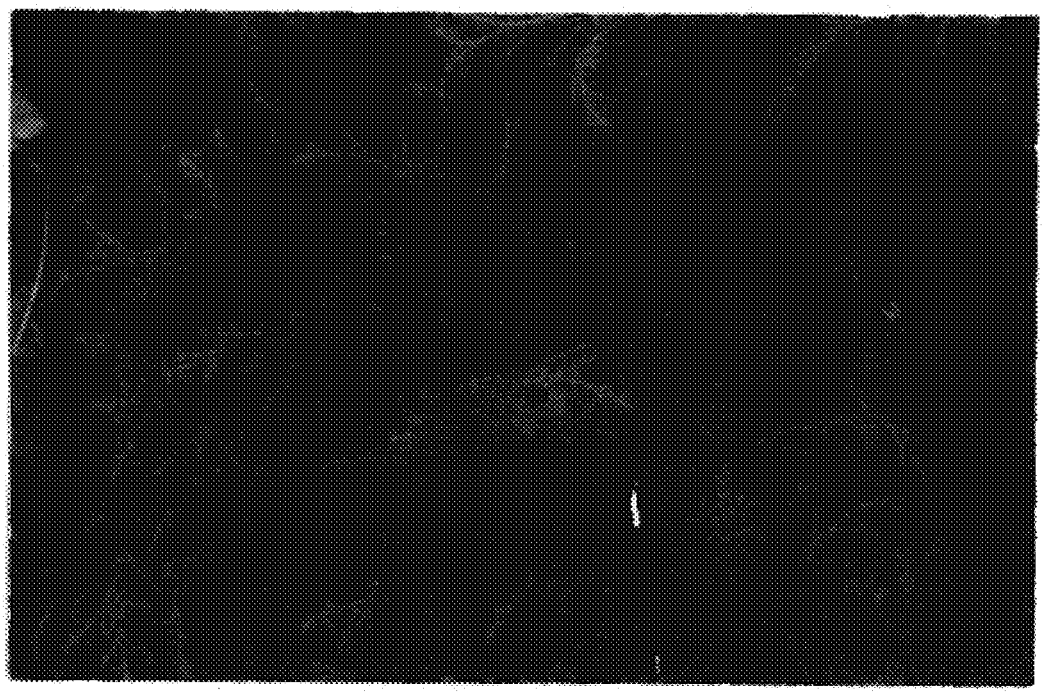
FIG. 2 shows a close view of the fuzzy foliage of the new cultivar during the winter wherein such foliage has assumed a greyed-orange coloration.
Figure 3:
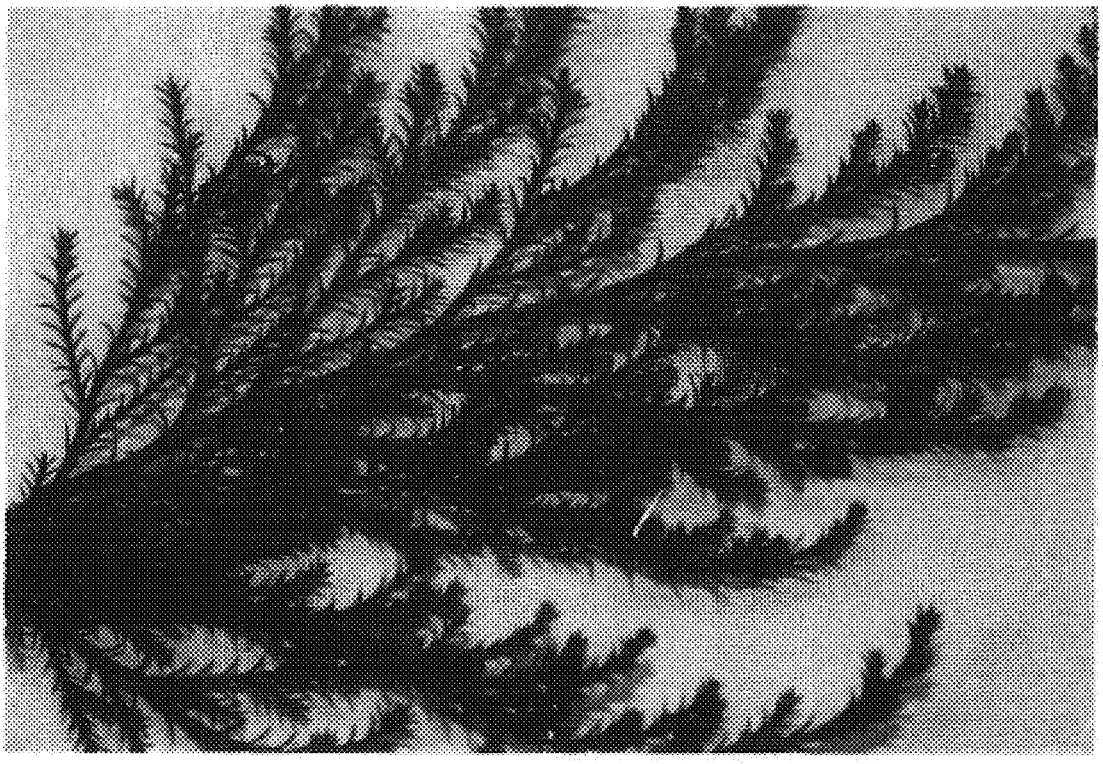
FIG. 3 shows an even closer view of the fuzzy foliage of the new cultivar during the winter. The distinctive substantially raised leaf scales of the new cultivar are illustrated.
Figure 4:
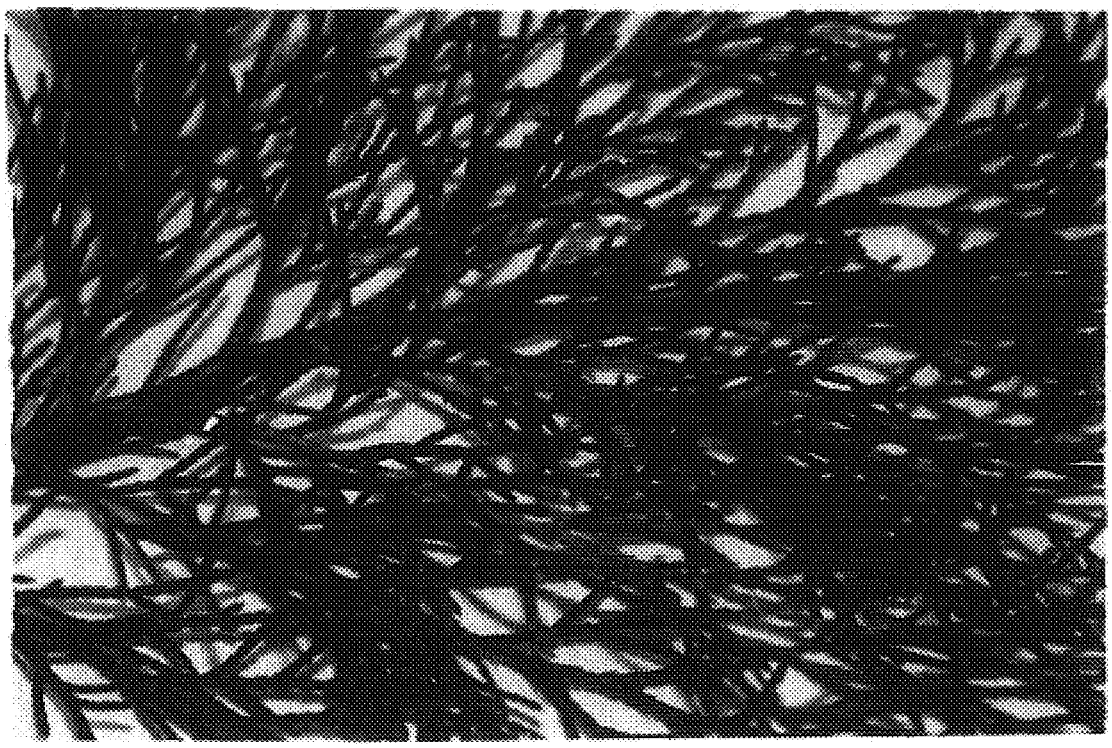
FIG. 4 shows for comparative purposes typical foliage of the *Microbiota decussata* parent plant wherein typical appressed leaf scales are illustrated.

The following is a detailed description of the new cultivar of the present invention which was prepared while observing primarily during mid-November 2007 approximately five year-old container-grown plants at West Grove, Pa., U.S.A., which had been reproduced by the rooting of cuttings. For the first five to six months the plants had been grown indoors during which time root development took place. The plants next had been placed in larger containers and were grown outdoors with protection of a sheet of plastic during the winter. Color terminology is in accordance with the R.H.S. Colour Chart of The Royal Horticultural Society, London, England, except where general color terms are used which are to be accorded their customary dictionary significance.

Type: Evergreen shrub with a low crown.

Plant:

*Growth habit.*—Low-growing, creeping, generally prostrate.

*Height.*—Commonly approximately 12 inches.

*Width.*—Commonly approximately 24 inches, and sometimes more.

*Twig presentation.*—Substantially horizontal.

*Mature branch presentation.*—Substantially horizontal.

*Twig color.*—Greyed-Orange Group 167A.

*Young branch color.*—Greyed-Orange Group 165A.

*Mature branch color.*—Grey Group 201A.

*Twig diameter.*—Commonly approximately 1.5 mm on average.

*Main branch diameter.*—Commonly approximately 8 mm on average.

*Secondary branch diameter.*—Commonly approximately 2.5 mm on average.

*Twig length.*—Commonly approximately 7 to 10 cm on average.

*Main branch length.*—Commonly up to approximately 20 cm.

*Secondary branch length.*—Commonly approximately 12 cm on average.

*Twig textures.*—Generally smooth except for leaves which are borne singly at a spacing of approximately 5 mm.

*Main branch texture.*—Somewhat rough.

*Secondary branch texture.*—Somewhat rough with many leaves which are borne singly at a spacing of approximately 5 mm.

*Degree of branching.*—Medium dense.

Foliage:

*Arrangement.*—Branchlets in fuzzy sprays when juvenile and when mature.

*Length.*—Commonly approximately 4.5 mm on average.

*Width.*—Commonly approximately 1 mm on average.

*Base.*—Truncate.

*Apex.*—Acuminate.

*Margin.*—Entire.

*Texture.*—Smooth on upper and under surfaces.

*Summer color.*—Green Group 137C on upper and under surfaces.

*Winter color.*—Greyed-Orange Group 177C on upper and under surfaces.

*Fragrance.*—Somewhat resembles resin when rubbed or when cut.

Inflorescence:

*Cones.*—None observed to date.

*Seeds.*—None observed to date.

Development:

*Hardiness.*—U.S.D.A. Hardiness Zone Nos. 3 to 8.

*Propagation protocol.*—Asexually reproduces well during the winter by the use of cuttings with the aid of Hormodin No. 3 rooting hormone and bottom heating at 70° F.

*Disease resistance.*—No particular susceptibility has been noted during observations to date.

*Pest resistance.*—No particular susceptibility has been noted during observations to date.

*Usage.*—Ornamental for growing as a specimen plant or as a ground cover.

Plants of the new 'Condavis' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct Siberian Cypress plant possessing the following characteristics:

(a) displays a creeping prostrate growth habit, (b) forms attractive green foliage wherein the leaf scales are raised so as to impart a fuzzy appearance unlike the appressed leaf scales displayed by common *Microbiota decussata* plants, and (c) is well suited for growing as a specimen plant or in a group as a ground cover;

substantially as illustrated and described.

* * * * *